Oct. 11, 1932. A. B. SHAW Plant Pat. 34
CARNATION
Filed March 19, 1932
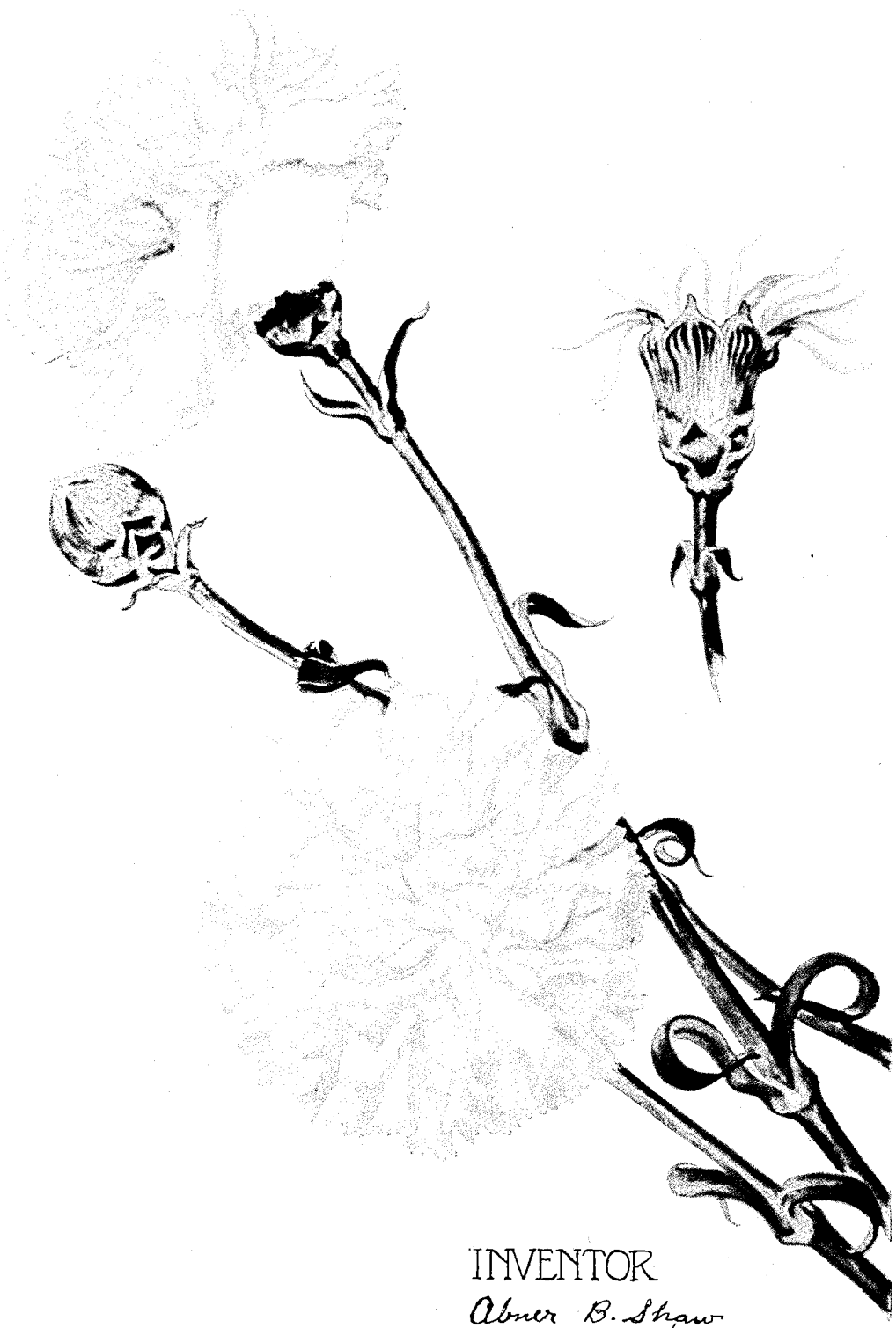
INVENTOR
Abner B. Shaw
Orville M Kile
PLANT·PATENT·AGENT Patented Oct. 11, 1932

Plant Pat. 34

UNITED STATES PATENT OFFICE

ABNER B. SHAW, OF NORTH DARTMOUTH, MASSACHUSETTS, ASSIGNOR TO STEPHEN E. SHAW, OF NORTH DARTMOUTH, MASSACHUSETTS

CARNATION

Application filed March 19, 1932. Serial No. 599,954.

My invention relates to improvements in fragrant, deep pink or red carnations of the type ordinarily designated as perpetual blooming or greenhouse cutting carnations. The object of my improvement is to provide a deep pink or red carnation of the type indicated having larger size, a more nearly perfect form, a pleasing and distinctive shade of color, superior habits of growth and various other characters which make it useful and valuable.

This new carnation is the result of the cross breeding of the two well-known varieties Betty Lou and Eldora. Some of the characters of each of the parent varieties are shown in this new variety but in addition certain valuable characters have been so emphasized in the offspring as to cause the latter to bear little resemblance to either of the parent varieties.

This successful cross was made by me early in the year 1928 and the first blossoms were noted and observed during the winter of 1928–29. The superior qualities of this seedling being then apparent, I immediately took steps to reproduce this variety by the usual method of making and rooting cuttings. During the season 1930–31 I produced twelve plants of this variety thus proving its ability to reproduce successfully. Since that date I have further materially multiplied my stock of this variety but it has not yet been offered for sale or otherwise distributed.

The accompanying illustrations show in full color a full front view of the blossom, a side view of same, a tightly closed bud, a detailed view of the calyx cup, and some of the stems and leaves. It is not deemed necessary to show the plant as a whole although it is to be distinctly understood that my claims cover the entire plant as well as its blossoms.

The following is a detailed description of this new variety of carnation:

An upright, vigorous growing plant 3 to 3½ feet high, having extra stout stems and only a moderate number of side branches or shoots arising from the nodes; notably free from such common plant diseases as "branch rot" and "blight."

Flowers: very large usually measuring 3¾ to 4 inches across, when grown under good greenhouse conditions. The number of petals in February runs 48 to 50 with only one or two rudimentary petals in each mature flower. The outer larger petals measure 2¼ to 2½ inches in length; edges are moderately serrated and crinkled but only a few of the more central petals are longitudinally curled. The flower is notably perfect in form, having a full high center and from a full front view the outer edges of the outer petals form almost a perfect circle.

Two pinkish tinted styles arise from the ovary but these are not visible in the flower unless the central petals are spread back artificially. One or both of these styles in the mature flower are usually split, thus giving the appearance of having either three or four styles. Only a few small anther-like bodies are found and these are not borne upon stamens but are attached as peculiar appendages from a few of the smaller petals at the throat of the flower, or at about the level of the tops of the styles.

The dominant color effect is approximately "rose red" as shown in Plate XII of Ridgeway's Color Standard and Nomenclature, edition of 1912. There are, however, touches of the brighter shade "Tyrian red" (Plate XII, same chart) on the outer edges of some of the petals when the blossom is in its prime. The under sides of the petals as well as the lightest visible portions of the upper sides of the petals may best be described as "rose" colored (a shade of pink, also shown in Plate XII of the Ridgeway Color Standard). Each petal is of a brighter and more pronounced shade on its upper surface than its lower surface and at its outer edge as compared with the central portion. Each petal is, of course, almost white on the narrow lower (and ordinarily invisible) portion reaching down into the throat of the flower. As the flower ages the outer edges of the petals become somewhat darker but they do not change to an undesirable purple as so frequently occurs in other varieties of pink or red carnations.

The flower has a distinct but mild odor.

*Calyx.*—The calyx is strong and tough in structure. It consists of a single tube 1¼ inches long, made up of five subdivisions or lips separated at the top by moderately deep cuts. This gives a spreading or open mouth effect which is one of the principal safeguards against bursting. This is a matter of importance in a carnation as large and heavy as this variety. As a further aid to prevent splitting or bursting, each lip of the calyx cup is provided with a humped spring-like development which while tending to hold the flower together, gives the necessary elasticity to prevent bursting. It is a notable fact that not a single case of splitting or bursting of the flower of this new variety has yet been found.

*Buds.*—Distinctive in shape, being blunt and heavy, almost spherical in shape as compared with the usual long pointed buds of other varieties.

*Stems and foliage.*—Of medium length and extra heavy and strong; approximately "empire green" in color (Plate XXXII Ridgeway's Color Standard and Nomenclature), overlaid with a heavy gray bloom. The leaves are smooth and inclined to be short. They are straight or only slightly curled when growing, but curl extensively when cut and kept at room temperatures.

This variety does not produce an abundance of shoots, suitable for cuttings, arising from the nodes. This tendency toward slower reproduction is outweighed, however, by the certainty and ease with which the available cuttings take root and grow.

It is to be understood that the foregoing describes this new variety as it grows typically in the latitude of Boston, Massachusetts, but that there will be some variations in characters as between individual specimens particularly where grown under different conditions of soil, climate and treatment.

The more important characters which when considered either singly or in combination clearly distinguish my new carnation from all other known varieties are:

First, the distinctive and pleasing color of its blossoms.

Second, the unusually large size and perfect form of the blossoms.

Third, the mild rather than strong odor.

Fourth, the light pink styles, two in number and with split tops, and the rudimentary anthers with their peculiar mode of suspension from the petals.

Fifth, the strong, heavy green stems of medium length, bearing leaves rather short in length.

Sixth, the strong calyx cup, equipped with spring-like lips and so constructed as to prevent splitting or bursting.

Seventh, the blunt, rounded, heavy buds.

Eighth, the vigorous growth, minimum of side shoots and the ease with which cuttings take root.

Ninth, apparent freedom from and resistance to plant diseases common to most varieties of carnations.

I claim:

The variety of carnation herein shown and described characterized particularly by its deep pink or red color tones, its large size and almost perfect form, its strong stem and calyx cup which prevents bursting, its vigorous growth and freedom from disease.

In testimony whereof I affix my signature.

ABNER B. SHAW.